United States Patent

Hydes

[11] 4,329,299
[45] May 11, 1982

[54] COMPOSITION OF MATTER CONTAINING PLATINUM

[75] Inventor: Paul C. Hydes, Reading, England

[73] Assignee: Johnson, Matthey & Co., Limited, London, England

[21] Appl. No.: 179,786

[22] Filed: Aug. 20, 1980

[30] Foreign Application Priority Data

Aug. 23, 1979 [GB] United Kingdom ................. 7929442

[51] Int. Cl.³ .............................................. C07F 15/00
[52] U.S. Cl. .................................. 260/429 R; 424/287
[58] Field of Search .................................... 260/429 R

[56] References Cited

PUBLICATIONS

Tobe et al., Clinical Hemotology & Oncology, vol. 7, No. 1, pp. 115-120 and 127-134.
Braddock et al., Chemico-Biological Interactions (Amsterdam) vol. 11, No. 3, pp. 145-147, 149, 150, 152-159 and 161, (1975).

Primary Examiner—Helen M. S. Sneed
Attorney, Agent, or Firm—Cushman, Darby & Cushman

[57] ABSTRACT

Compositions of matter suitable for the treatment of cancer comprise platinum co-ordination compounds having the general formula

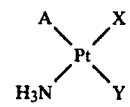

or

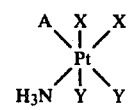

in which A is a straight-chain, branched chain or cyclic aliphatic amine, X and Y are halogen and the Z groups are halogen or hydroxy.

2 Claims, No Drawings

COMPOSITION OF MATTER CONTAINING PLATINUM

This invention relates to platinum co-ordination compounds and to pharmaceutical compositions containing them.

The use of certain co-ordination compounds of platinum in the treatment of cancer is now becoming accepted as a standard therapeutic technique, the best-known compound for this purpose so far being cis-diammine-dichloroplatinum (II). This compound has activity against a broad spectrum of tumours but has unpleasant side effects.

In the search for a suitable replacement for the above compound, i.e. one which has higher activity and/or lower toxicity, many analogous compounds have been prepared and tested. Most of these compounds have corresponded with either general formula $Pt(II)A_2X_2$ or general formula $Pt(IV)A_2X_2OH_2$ where X is an anion such as chloride and A is an amine and, in each such compound, the amine groups have been identical, although compounds where the amine groups have been selected from the same class of amines, for example branched chain amines, have been considered from a theoretical stand point.

We have now found that it is possible to prepare complexes of platinum (II) and platinum (IV) including amine groups where the amine groups are different and that these complexes give promising results compared with cis-diammine-dichloroplatinum (II).

According to a first aspect of the present invention, therefore, a composition of matter comprises a cis co-ordination compound of platinum, (II) having the structure

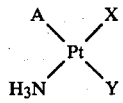

or a cis-trans co-ordination of platinum (IV) having the structure

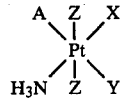

in which A is an amine having the formula $R-NH_2$ where R is substituted or unsubstituted straight-chain alkyl, substituted or unsubstituted branched-chain alkyl or substituted or unsubstituted cyclic alkyl, X and Y are the same or different halogen and the Z groups are either halogen or hydroxy.

Straight chain aliphatic amines have the general formula

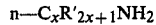

in which x is an integer from 1 to 9 inclusive and the R' groups are the same or different and are selected from hydrogen, substituted or unsubstituted aryl, cycloalkyl, cycloalkenyl, alkoxy and aryloxy, halogen, pseudohalogen, hydroxy, carbonyl, formyl, nitro, amino, acylamino, sulphonic acid and salts thereof and carboxylic acid and salts and esters thereof.

Branched chain aliphatic amines have the general formula

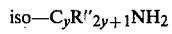

in which y is an integer from 3 to 9 inclusive and the R'' groups are the same or different and are selected from hydrogen, substituted or unsubstituted alkyl, aryl, alkenyl, cycloalkyl, cycloalkenyl, alkoxy and aryloxy, halogen, pseudohalogen, hydroxy, carbonyl, formyl, nitro, amino, acylamino, sulphonic acid and salts thereof and carboxylic acid and salts and esters thereof.

Cyclic alkylamines have the general formula

in which z is an integer from 3 to 7 inclusive and the R''' groups are the same or different and are selected from hydrogen, substituted or unsubstituted alkyl, aryl, alkenyl, cycloalkyl, cycloalkenyl, alkoxy and aryloxy, halogen, pseudohalogen, hydroxy, carbonyl, formyl, nitro, amino, acylamino, sulphonic acid and salts thereof and carboxylic acid and salts and esters thereof.

Preferably, the R', R'' and R''' groups are all hydrogen but, where one or more of them is other than hydrogen, it can be a lower alkyl, for example, methyl or ethyl, or a solubilising group, for example, an acid or salt thereof. Where a solubilising group is used in the form of a salt, the salt can be, for example, the sodium, potassium or lithium salt, where conditions are appropriate and the clinical conditions require high solubility. We intend the above definition of the R', R'' and R''' groups also to include oxygen and sulphur, such that one doubly-bonded oxygen or sulphur atom is represented by two R groups.

Examples of particular compounds according to the invention are cis-dichloroammine-isopropylamine-platinum (II), cis-dichloroammine-ethylamine-platinum (II), cis-dichloroammine-cyclopentylam ine-platinum (II) and the corresponding platinum (IV) species with trans-halo or trans-OH groups.

The term "pseduohalogen" in this specification has the meaning given on p560 of "Advanced Inorganic Chemistry" by Cotton and Wilkinson, Interscience Publishers, 1966, as being "a molecule consisting of more than two electro-negative atoms which, in the free state, resembles the halogens; these pseudohalogens give rise to anions which resemble the halide ions in behaviour". Examples of suitable halogens are cyanate, thiocyanate and azide.

The term "cis" as applied to the compounds of the invention indicates that A cannot be in a position trans to B and that X cannot be in a position trans to Y. The term "trans", when applied to the platinum (IV) compound of the invention as defined, indicates that the two Z groups are respectively above and below the A-B-X-Y plane of the molecule.

Normally the compound is used in association with a pharmaceutically acceptable carrier therefore. Accordingly, in a second aspect, the present invention provides a pharmaceutical composition which comprises a compound according to the first aspect of the invention and a pharmaceutically-acceptable carrier for said compound; these compositions can be formulated so as to be suitable, for example, for parenteral or oral administration to animals.

The synthesis of compounds according to the invention gives low overall yields owing to the many stages involved. They all start from the complex K[PtCl$_3$(NH$_3$)] which is itself prepared from cis-[PtCl$_2$(NH$_3$)$_2$] and yields in the final stage range from 20–40%. A common feature of the preparations is that a black precipitate forms in the reaction mixture within 16 hours of mixing the reagents and has all the appearance of a decomposition to platinum metal. However, unlike colloidal Pt, the isolated solid dissolves completely in DMF and passes through a sinter as a black solution which yields a white solid and red liquor on treatment with HCl.

The preparation of two complexes according to the invention will now be described by way of example.

(i) Preparation of Amminedi chloroisopropylamineplatinum (II)

[PtCl$_2$(NH$_3$)(i-C$_3$H$_7$NH$_2$)]

Isopropylamine (1.38 g, 0.024 mol. 2. 0ml) was mixed with ca. 5 ml of water and added to a stirred solution of K[PtCl$_3$(NH$_3$)](8.5 g, 0.024 mol.) in water (30 ml). The red solution was placed in a refrigerator overnight to give a black precipitate. The mixture was kept for a total of 3 days at 0° C., and then the solid was filtered off on a porosity 3 sinter, washed with water and ethanol and air dried to give a black and green mixture of solids. (The aqueous washings were black).

Crude yield = 2.8 g (34%)

The crude product was ground in a mortar to give a light grey powder. This was stirred with DMF (7 ml) and charcoal, and the solution was filtered through a porosity 4 sinter. HCl (50%, 7 ml) was added to the black filtrate to give a red solution and a yellow precipitate. The mixture was kept at 5° C. for 30 minutes, filtered and washed with HCl (50%) and ethanol and air dried to give a yellow product.

Yield = 1.2 g

The product (1.1 g) was recrystallised again from DMF/HCl (50%) but without using charcoal.

Yield = 0.6 g (overall yield = 7.3%)

| Assay: | Pt | C | H | N | Cl |
|---|---|---|---|---|---|
| Calculated % | 57.0 | 10.5 | 3.5 | 8.2 | 20.7 |
| Found % | — | 11.0 | 3.7 | 8.8 | — |

Infra-red spectrum:

The nitrogen-hydrogen stretching modes occur at 3300, 3270, 3200 and 3120 cm$^{-1}$.

(ii) Preparation of cis-Amminecyclopentylaminedichloroplatinum(II) cis-[PtCl$_2$(NH$_3$)(cyclo-C$_5$H$_9$NH$_2$)]

Cyclopentylamine (4.3 ml, 0.044 mol.) was pipetted directly into a solution of K[PtCl$_3$(NH$_3$)] (0.046 mol) in water (65 ml) in a 100 ml beaker. The red solution was stored at 5° C. in the dark for 4 days and the solid filtered off, washed with water and ethanol and air dried. Yield = 1 g. The recrystallisation was repeated with DMF (5 ml) and 1:1 HCl (6 ml) to give a pale yellow solid.

Yield = 0.8 g (overall yield = 4.8%).

| Assay: | Pt | C | H | N | Cl |
|---|---|---|---|---|---|
| Calculated % | 53.0 | 16.3 | 3.8 | 7.6 | 19.3 |
| Found % | — | 16.4 | 3.8 | 7.3 | — |

Infra-red spectrum:

The nitrogen-hydrogen stretching modes occur at 3290, 3250, 3220 and 3140 cm$^{-1}$.

Compounds according to the invention were tested against ADJ/PC6A solid tumour and against L1210 Leukaemia in mice. In the results which follow, LD$_{50}$ is a measure of toxicity and denotes the lethal dose in mgms/kilo body weight which killed 50%, of the samle and ID$_{90}$ is a measure of activity against the tumour concerned and denotes the dose which caused a 90% by weight tumour inhibition. The therapeutic index (TI) is the ratio of LD$_{50}$ to ID$_{90}$ and indicates the selectivity of the compound. For solid tumours the amount of inhibition is measured by a comparison of the weights of treated and untreated (control) tumours. This is expressed as a percentage and termed T/C. For leukaemias the mean survival time is compared with that of the controls, and any increase in life span is a measure of anti-tumour activity and is quoted as T/C %.

For ADJ/PC6A tumour, the tumour was implanted subcutaneously in female Balb/C mice and treatment was commenced 24 days later using a suspension of the complexes in arachis oil. For L1210 leukaemia, 10$^5$–10$^6$ cells were implanted intraperitoneally in female BDF$_1$ mice and the compound was also administered intraperitoneally in saline.

The following Tables give the results obtained. For testing against ADJ/PC6A tumour, results are compared with cis-dichlorodiammineplatinum(II). For L1210 leukaemia, daily doses were administered for 9 days.

TABLE 1

| | ADJ/PC6A tumour | | |
|---|---|---|---|
| Compound | ID$_{90}$ | LD$_{50}$ | TI |
| cis-[PtCl$_2$(NH$_3$)(C$_2$H$_5$NH$_2$)] | 0.9 | 11.3 | 12 |
| cis-[PtCl$_2$(NH$_3$)(cyclo-C$_5$H$_9$NH$_2$)] | 0.5 | 11.3 | 25 |
| cis-[PtCl$_2$(NH$_3$)$_2$] (prior art) | 1.6 | 13.0 | 8 |

TABLE 2

| | L1210 Leukaemia. | |
|---|---|---|
| Compound | Dose (mg . kilo$^{-1}$) | T/C % |
| cis-[PtCl$_2$(NH$_3$)(C$_2$H$_5$NH$_2$)] | Single 6 | 143 |
| | Daily 3 | 171 |
| cis-[PtCl$_2$(NH$_3$)(i-C$_3$H$_7$NH$_2$)] | Single 3 | 150 |
| | Daily 1.5 | 171 |
| cis-[PtCl$_2$(NH$_3$)(cyclo-C$_5$H$_9$NH$_2$)] | Single 3 | 150 |
| | Daily 1.5 | 193 |

Complexes according to the invention are seen to have a high degree of activity against the tumours tested and are less toxic than cis-dichlorodiammine platinum (II). In addition, white blood cell counts and blood urea nitrogen levels, although initially detrimentally affected, showed a recovery trend over 7 days.

I claim:

1. A composition of matter comprising a cis co-ordination compound of platinum (II) having the structure

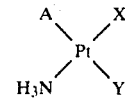

in which A is an amine having the formula R-NH$_2$ where R is branched chain alkyl, X and Y are the same or different halogen.

2. A composition according to claim 1 which is a cis co-ordination compound of platinum (II) wherein A is isopropylamine and X and Y are both chlorine.